United States Patent [19]

Sandstrom et al.

[11] Patent Number: 5,134,184
[45] Date of Patent: Jul. 28, 1992

[54] ROSIN MONOMALEIMIDES

[75] Inventors: Paul H. Sandstrom; Lawson G. Wideman, both of Tallmadge, Ohio

[73] Assignee: The Goodyear Tire & Rubber Company, Akron, Ohio

[21] Appl. No.: 572,826

[22] Filed: Aug. 27, 1990

[51] Int. Cl.$^5$ .............................. C08L 1/00; C08L 7/00
[52] U.S. Cl. .................................. 524/270; 530/210; 530/214; 530/221
[58] Field of Search ............... 524/270, 271, 272, 273, 524/274; 530/210, 211, 214, 215, 220, 221

[56] References Cited

U.S. PATENT DOCUMENTS 4,670,516  6/1987  Sackmann et al. ............... 525/327.6

*Primary Examiner*—John Kight, III
*Assistant Examiner*—Richard Jones
*Attorney, Agent, or Firm*—Bruce J. Hendricks

[57] ABSTRACT

The present invention relates to rosin monomaleimides which are useful as a total or partial replacement for extender or processing oil in rubber formulations. Addition of the rosin monomaleimides improve peel adhesion in rubber compositions. The rosin monomaleimides are prepared by reacting abietylamine and/or dehydroabietylamide with maleic anhydride.

7 Claims, No Drawings

ROSIN MONOMALEIMIDES

BACKGROUND OF THE INVENTION

Both natural and synthetic elastomers usually require the use of processing aids to assist mechanical breakdown and compounding. Materials such as mixtures of oil soluble sulfonic acids of high molecular weight with a high boiling alcohol, paraffin oils, blends of sulfonated petroleum products and selected mineral oils are conventionally used as processing aids. Additional examples include petroleum, paraffinic and vegetable oils, coal tar, petroleum residues or pitches and naturally occurring or synthetic resins.

One advantage in using processing aids is they assist the incorporation of fillers and other ingredients with low power consumption since they reduce internal friction in calendering and extrusion. By reducing the amount of friction during compounding, the temperature of the rubber will remain lower and thus minimize the possibility of scorch.

Various types of rosin acids have been used as extenders for high molecular weight SBR. See *Properties of GR-S Extended With Rosin Type Acids*, L. H. Howland, J. A. Reynolds, and R. L. Provost, Industrial and Engineering Chemistry, Vol. 45, No. 5, May 1953. Whereas reasonably good cured physical properties can be obtained with the rosin type acids, there are problems associated with their use which include cure retardation, high tack and poor low temperature performance, which limit their use as an extender in rubber formulations.

U.S. Pat. No. 4,478,993 discloses the use of decarboxylated rosin acid also known as thermal oil as a total or partial replacement for oil in a rubber formulation. Compared with the use of aromatic extending oils in rubbers, decarboxylated rosin acids provide comparable processing and low temperature performance and superior abrasive resistance.

SUMMARY OF THE INVENTION

The present invention relates to (a) a rosin monomaleimides of the formula:

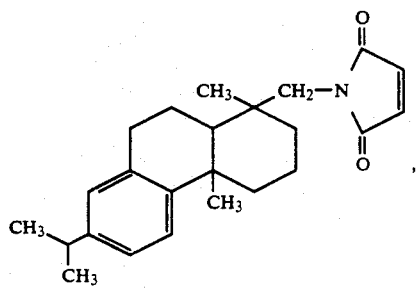

-continued

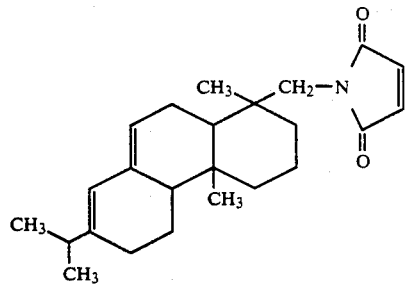

or mixtures thereof, and (b) a rubber selected from the group consisting of natural rubber, homopolymers of conjugated dienes and copolymers of conjugated dienes and ethylenically unsaturated monomers.

DETAILED DESCRIPTION OF THE INVENTION

There is also disclosed a process for preparing rubber compositions which comprises admixing a rubber selected from the group consisting of natural rubber, homopolymers of conjugated diolefins, copolymers of conjugated diolefins and ethylenically unsaturated monomers or mixtures thereof with a rosin monomaleimide.

There is also disclosed a rubber composition which comprises (1) a rubber selected from the group consisting of natural rubber, homopolymers of conjugated diolefins, copolymers of conjugated diolefins and ethylenically unsaturated monomers or mixtures thereof and a rosin monomaleimide of the formula:

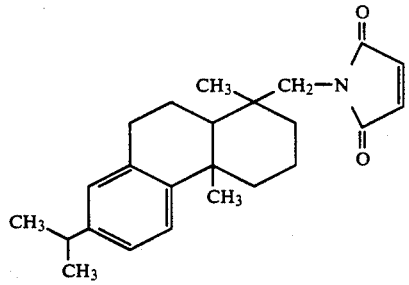

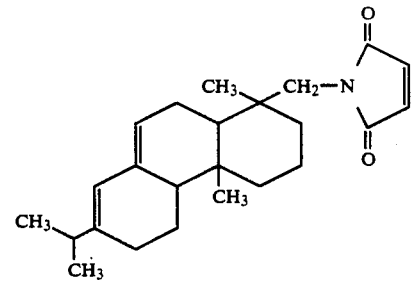

or mixtures thereof.

The rosin monomaleimide is prepared by reacting abietylamine or dehydroabietylamine with maleic anhydride. The abietylamine and dehydroabietylamine are derived from rosin. Rosin is a solid resinous material that occurs naturally in pine trees. The three major sources of rosin are gum rosin, wood rosin and tall oil rosin. Gum rosin is from the oleoresin extrudate of the living pine tree. Wood rosin is from the oleoresin contained in the aged stumps. Tall oil rosin is from the waste liquor recovered as a by-product in the Kraft paper industry.

The aged virgin pine stump is the source of wood rosin. The stump is allowed to remain in the ground for about ten years so that its bark and sapwood may decay and slough off to leave the heartwood rich in resin. It is known that production of pine stump rosin can be artificially stimulated by injecting the herbicide, Paraquat, into the lower portion of the tree. This treatment of the stump produces Pinex TM rosin.

Rosins derived from both oleoresin and aged stump wood are composed of approximately 90% resin acids and 10% nonacidic components. Chemical treatment of rosins, such as hydrogenation, dehydrogenation, or polymerization are known which produce modified resins.

Maleic anhydride is reacted with abietylamine or dehydroabietylamine under suitable conditions to form a compound having a rosin moiety connected to a maleimide moiety. Dehydroabietylamine in a 90% purity is commercially available from Aldrich Chemical Company. Abietylamine and dehydroabietylamine can be used individually or more commonly in mixtures with various amounts of other rosin amines including levopimarylamine, neoabietylamine, palustrylamine, tetrahydroabietylamine, pimarylamine, isopimarylamine, $\Delta$-isopimarylamine, elliotinoylamine and sandaracopimarylamine. Therefore, in connection with the above formula, the rosin monomaleimide may also be derived from use of the above amines which are commonly found in admixture with abietylamine and/or dehydroabietylamine.

The maleic anhydride may be reacted with the abietylamine and/or dehydroabietylamine in a variety of mole ratios. Generally the mole ratio of maleic anhydride to abietylamine and/or dehydroabietylamine ranges from about 1.5:1 to about 0.75:1 with a range of from about 1.1:1 to about 0.9:1 being preferred.

An organic solvent may be used to dissolve the abietylamine or dehydroabietylamine. The solvent is preferably inert to the reaction between the maleic anhydride and the abietylamine and/or dehydroabietylamine. Illustrative of solvents suitable for use in the practice of this invention include: saturated and aromatic hydrocarbons, e.g., hexane, octane, dodecane, naphtha, decalin, tetrahydronaphthalene, kerosene, mineral oil, cyclohexane, cycloheptane, alkyl cycloalkane, benzene, toluene, xylene, alkyl-naphthalene, and the like; ethers such as tetrahydrofuran, tetrahydropyran, diethylether, 1,2-dimethoxybenzene, 1,2-diethoxybenzene, the mono- and dialkylethers of ethylene glycol, propylene glycol, butylene glycol, diethylene glycol, dipropylene glycol, oxyethyleneoxypropylene glycol, and the like; fluorinated hydrocarbons that are inert under the reaction conditions such as perfluoroethane, monofluorobenzene, and the like. Another class of solvents are sulfones such as dimethylsulfone, diethylsulfone, diphenolsulfone, sulfolane, and the like. Mixtures of the aforementioned solvents may be employed so long as they are compatible with each other under the conditions of the reaction and will adequately dissolve the abietylamine or dehydroabietylamine and not interfere with the reaction.

The reaction between the maleic anhydride and abietylamine and/or the dehydroabietylamine may be conducted in the presence of a catalyst to speed up the reaction. Examples of catalysts that may be used include acid catalysts such as sulfuric acid, hydrochloric acid and toluenesulfonic acid. The amount of catalyst that may be used will vary depending on the particular catalyst that is selected. For example, when an acid catalyst is used, from about 5% to about 10% by weight of the abietylamine and/or dehydroabietylamine is recommended.

The reaction between the maleic anhydride and abietylamine and/or dehydroabietylamine may be conducted over wide temperatures. The temperatures may range from moderate to an elevated temperature. In general, the reaction may be conducted at a temperature of between about 100° C. to about 250° C. The preferred temperature range is from about 200° C. to about 240° C., while the most preferred temperature range is from about 210° C. to about 220° C.

The reaction may be conducted under a variety of pressures. Pressures ranging from about 0 psig to about 100 psig may be used to conduct the reaction.

The reaction is conducted for a period of time sufficient to produce the desired rosin monomaleimide. In general, the reaction time can vary from minutes to several hours. If the more sluggish reaction conditions are selected, then the reaction time will have to be extended until the desired product is produced. It is appreciated that the residence time of the reactants will be influenced by the reaction temperature, concentration and choice of catalyst, total gas pressure, partial pressure exerted by its components, concentration and choice of solvent, and other factors. Desirably, the reaction is conducted until a molar equivalent of water has been removed.

The process for the preparation of the rosin monomaleimide may be carried out in a batch, semicontinuous or continuous manner. The reaction may be conducted in a single reaction zone or in a plurality of reaction zones, in series or in parallel. The reaction may be conducted intermittently or continuously in an elongated tubular zone or in a series of such zones. The material of construction of the equipment should be such as to be inert during the reaction. The equipment should also be able to withstand the reaction temperatures and pressures. The reaction zone can be fitted with internal and/or external heat exchangers to control temperature fluctuations. Preferably, an agitation means is available to ensure the uniform reaction. Mixing induced by vibration, shaker, stirrer, rotating, oscillation, etc. are all illustrative of the types of agitation means which are contemplated for use in preparing the composition of the present invention. Such agitation means are available and well known to those skilled in the art.

Addition of the rosin monomaleimide to sulfur vulcanizable elastomers as a processing oil surprisingly enhances the adhesion properties of the vulcanizate. The term "rubber" or "elastomer" as used herein embraces both natural rubber and all its various raw and reclaim forms as well as various synthetic rubbers. Representative synthetic elastomers are the homopolymerization products of butadiene and its homologues and derivatives, as for example, methylbutadiene, dimethylbutadiene, chloroprene (neoprene synthetic rubber) and pentadiene as well as copolymers such as those formed from butadiene or its homologues or derivatives with other unsaturated organic compounds. Among the latter are acetylenes, e.g., vinyl acetylene: olefins, for example, isobutylene, which copolymerizes with isoprene to form butyl rubber: vinyl compounds, for example vinylchloride, acrylic acid, acrylonitrile (which polymerizes with butadiene to form NBR), methacrylic acid and styrene, the latter compound polymerizing with butadiene to form SBR, as well as vinyl esters and various unsaturated aldehydes, ketones and ethers, e.g., acrolein, methyl isopropenyl ketone and vinylethyl ether. Also included are the various synthetic rubbers prepared by the homopolymerization of isoprene and the copolymerization of isoprene with other diolefins and various unsaturated organic compounds. Additionally, included are the synthetic rubbers such as 1,4-cis polybutadiene and 1,4-cis polyisoprene and similar synthetic rubbers such as EPDM. The preferred rubbers for use with the rosin monomaleimide are natural rubber, polybutadiene, SBR and polyisoprene.

The rubber vulcanizates containing the rosin monomaleimide may be used in the preparation of tires, motor mounts, rubber bushings, power belts, printing rolls, rubber shoe heels and soles, rubber floor tiles, caster wheels, elastomer seals and gaskets, conveyor belt covers, wringers, hard rubber battery cases, automobile floor mats, mud flaps for trucks, ball mill liners, and the like.

The rosin monomaleimide may be used in a wide variety of proportions in the rubber and may be a substitute, in whole or part for conventional extender or process oils. By the term "extender or process oils", it is meant oils such as aromatic oils, naphthenic oils, paraffinic oils and the like as well as blends thereof. Specific examples of such oils include those largely composed of naphthenic and alkylated naphthenic hydrocarbons and mixtures thereof with various aromatic hydrocarbons. Such oils may be obtained from the high boiling fractions of the so-called naphthenic or mixed crude oils. They may comprise distillate fractions boiling above about 200° C. Suitable fractions are those at least 90 percent of which boil above about 250° C. as more volatile members may be lost during or after compounding and curing the rubber. Generally, the level of rosin monomaleimide that may be added to the rubber composition may range from about 1 phr (parts per hundred rubber) to about 50 phr. Preferably the amount of rosin monomaleimide that is added ranges from about 2 phr to about 35 phr.

The following examples are presented in order to illustrate but not limit the present invention.

Example 1

156 grams (approximately 0.5 mole) of dehydroabietylamine having a purity of 90(the remaining 10% was believed to be a mixture of rosin amines) was slowly added neat to a 1-liter round flask containing 49 grams of maleic anhydride dissolved in 138 ml of meta-xylene. The reaction temperature was maintained below 50° C. until the reaction exotherm subsided. The reaction mixture was then heated to a pot temperature of about 205° C. to 210° C. by adjusting the amount of xylene present (about 20 ml removed). The overhead water from the reaction was collected in a Dean-Stark trap. The acid catalyst, 11 grams of p-toluenesulfonic acid, was added after the initial exotherm stops. After drying, a yield of 203 grams of crude product was recovered. The melting point was approximately 140°–170° C.

Example 2

Rubber compositions containing the materials set out in Table I were prepared in a BR Banbury using two separate stages of addition. The sulfur and accelerators were added to the compounds during the second stage of mixing. The processing oils (naphthenic/paraffinic oil or the rosin monomaleimide) were added to the Banbury during the first stage of mixing. The processing oil was a mixture of naphthenic/paraffinic oils. The rosin monomaleimide was prepared in accordance with Example 1. Table II below sets out the physical data from the two samples.

Peel adhesion testing was done to determine the interfacial adhesion between the rubber formulations that were prepared. The peel adhesion was determined by pulling the compound away from itself at a right angle to the untorn test specimen with the two ends being pulled apart at a 180° angle to each other using an Instron machine. The area of contact was determined from placement of a Mylar sheet between the compounds during cure. A window in the Mylar allowed the two compounds to come into contact with each other during testing.

TABLE I

| Material | Parts By Weight | Banbury Stage |
|---|---|---|
| Natural Rubber | 40.00 | 1 |
| Polybutadiene | 60.00 | 1 |
| Processing Oil* | 5.00 | 1 |
| Carbon Black | 50.00 | 1 |
| Antiozonant/Antioxidant | 4.00 | 1 |
| Rosin/Fatty Acids | 3.00 | 1 |
| Wax | 1.50 | 1 |
| Zinc Oxide | 3.00 | 1 |
| Tackifier | 4.00 | 1 |
| Sulfur/Accelerator | 2.85 | 2 |

*Naphthenic/Paraffinic oil or rosin monomaleimide.

TABLE II

| Cure Behavior and Vulcanizate Properties | | |
|---|---|---|
| | Naphthenic/ Paraffinic Oil | Rosin Mono-Maleimide |
| Rheometer 150° C. | | |
| Max. Torque | 33.3 | 30.5 |
| Min. Torque | 9.4 | 9.4 |
| t90, minutes | 23.5 | 32.4 |
| t25, minutes | 8.0 | 9.1 |
| Stress Strain (original samples) | | |
| Tensile Strength (MPa) | 15.1 | 12.5 |
| Elongation at Break (%) | 646 | 615 |
| 300% Modulus (MPa) | 5.8 | 4.9 |
| Peel Adhesion, 95° C. (Newtons) | 73 | 115 |
| Dematttia Flex | | |
| Pierced (.08"), 6 hours flex | .44 inch | .08 inch |

As can be seen from the above data, the peel adhesion value of 115 for the compounds of the present invention is significantly higher than for the compound containing naphthenic/paraffinic oil. The higher peel adhesion values show increased adhesion of the cured rubber to itself which relates to improved tear resistance. The Dematttia flex results also show improvement when using the compound of the present invention. The rosin monomaleimide containing compounds showed no crack growth after 6 hours of flexing, whereas the control showed a crack length of 0.44 inches.

We claim:

1. A composition comprising (a) a rosin monomaleimide of the formula:

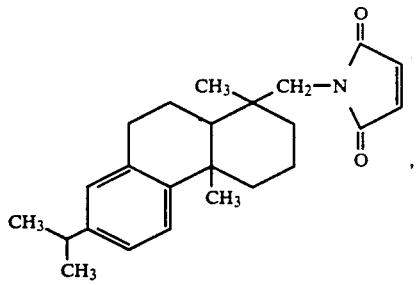

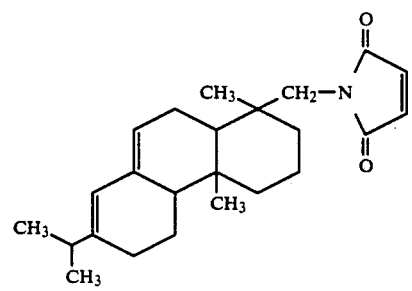

or mixtures thereof; and (b) a rubber selected from the group consisting of natural rubber homopolymers of conjugated dienes and copolymers of conjugated diolefins and ethylenically unsaturated monomers wherein said rosin monomaleimide is at a concentration of from about 1 part per hundred rubber to 50 parts per hundred rubber.

2. The process for preparing rubber compositions according to claim 1 wherein the rosin monomaleimide is at a concentration of from about 2 to 35 parts per hundred rubber.

3. The composition of claim 1 wherein said composition is at a concentration of from about 2 to 35 parts per hundred rubber.

4. The composition of claim 1 wherein the rosin monomaleimide is derived from dehydroabietyamine abietylamine, levopimarylamine, neoabietylamine, palustrylamine, tetrahydroabietylamine, pimarylamine, isopimarylamine, Δ-isopimarylamine, elliotinoylamine, sandaracompimarylamine or mixtures thereof.

5. A process for preparing rubber compositions which comprises admixing a rubber selected from the group consisting of natural rubber, homopolymers of conjugated diolefins, copolymers of conjugated diolefins and ethylenically unsaturated monomers or mixtures thereof with the rosin monomaleimide of the formula:

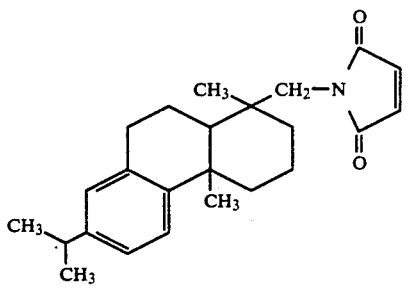

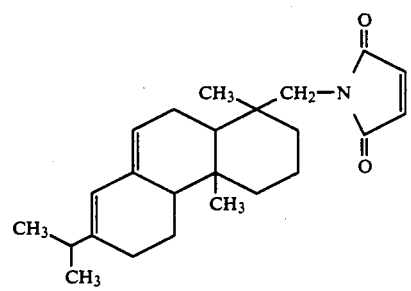

or mixtures thereof wherein said rosin monomaleimide is at a concentration of from about 1 part per hundred rubber to 50 parts per hundred rubber and is in an intimate mixture with said rubber.

6. The process of claim 5 wherein said rubber is selected from the group consisting of natural rubber, polybutadiene, SBR, polyisoprene and mixtures thereof.

7. The composition of claim 1 wherein said rubber is selected from the group consisting of natural rubber, polybutadiene, SBR, polyisoprene and mixtures thereof.

* * * * *